United States Patent [19]

Nakagawa et al.

[11] Patent Number: 5,322,685
[45] Date of Patent: Jun. 21, 1994

[54] SKIN CREAM PREPARATION FOR EXTERNAL USE

[75] Inventors: Akira Nakagawa; Satoru Miyata, both of Tosu; Yusuke Kubota, Dazaifu, all of Japan

[73] Assignee: Hisamitsu Pharmaceutical Co., Inc., Saga, Japan

[21] Appl. No.: 820,638

[22] PCT Filed: Jul. 27, 1990

[86] PCT No.: PCT/JP90/00965
   § 371 Date: Jan. 22, 1992
   § 102(e) Date: Jan. 22, 1992

[87] PCT Pub. No.: WO91/01716
   PCT Pub. Date: Feb. 21, 1991

[30] Foreign Application Priority Data

Aug. 3, 1989 [JP] Japan .................. 1-202338
Feb. 9, 1990 [JP] Japan .................. 2-31189

[51] Int. Cl.$^5$ .................. A61K 31/74; A61K 7/00
[52] U.S. Cl. .................. 424/78.03; 424/401; 514/938; 514/943; 514/975; 514/970

[58] Field of Search .................. 424/401, 70, 63; 514/784, 942, 943, 939, 946, 783

[56] References Cited

U.S. PATENT DOCUMENTS

| | | | |
|---|---|---|---|
| 4,216,201 | 8/1980 | Calvo | 424/63 |
| 4,348,415 | 9/1982 | Tsutsumi et al. | 424/70 |
| 4,425,329 | 1/1984 | Tsutsumi et al. | 514/784 |
| 4,751,241 | 6/1988 | Motoyama | 514/532 |
| 4,829,092 | 5/1989 | Nelson et al. | 514/873 |
| 4,882,359 | 11/1989 | Nakagawa et al. | 514/946 |

*Primary Examiner*—Thurman K. Page
*Assistant Examiner*—Sally Gardner
*Attorney, Agent, or Firm*—Bucknam and Archer

[57] ABSTRACT

A W/O skin cream preparation for external use useful as a remedy for skin diseases which consists of a cream base comprising a diglycerol fatty acid ester and/or a sorbitan fatty acid ester having an HLB value of from 3 to 7, a polyvalent metal salt of a saturated or unsaturated fatty acid having 10 to 22 carbon atoms, an inorganic or organic acid salt, an oily phase component, and water together with an active ingredient.

8 Claims, No Drawings

SKIN CREAM PREPARATION FOR EXTERNAL USE

TECHNICAL FIELD

This invention relates to a cream preparation for external use which contains a remedy for skin diseases as an active ingredient. More particularly, it relates to a W/O skin cream preparation for external use which contains a remedy for skin diseases, such as an antiinflammatory agent, an antibacterial agent or an antiallergic agent, as an active ingredient and is useful in treating, for example, eczema, dermatitis, prurigo, atopic dermatitis, psoriasis, candidiasis or trichophytia.

BACKGROUND ART

A W/O cream base which comprises an oily external phase and thus exerts an effect of protecting the skin is superior to an O/W one as a base for a remedy for skin diseases. However, O/W cream base preparations containing remedies for skin diseases have been often used hitherto, while W/O cream preparations have been scarcely employed. This is because the conventional W/O cream bases contain a large amount of oily phase components and thus are inferior to the O/W cream bases in the comfort in the use and the stability of preparation. When an active ingredient is blended with a W/O cream base of a high moisture content, in particular, the comfort in the use is improved but the heat stability of the preparation is deteriorated. Thus no satisfactory cream preparation has been obtained so far.

Examples of the prior art cream preparations containing ketotifen or its fumarate include Japanese Patent Application Laid-Open Gazette Nos. Sho. 51-32724, Sho. 51-142543, Sho. 62-164624, Hei. 1-102024 and Hei. 1-121218. However none of these cream preparations containing ketotifen or its fumarate disclosed in the above references is satisfactory from the viewpoints of the stability of the preparations and drug and the percutaneous absorption of the drug.

The conventional W/O cream base contains a very large amount of an oily phase, i.e., the external phase. When applied to the skin, therefore, it poorly dries and has a persistent stickiness, thus being uncomfortable. Furthermore, it is apt to cause liquid separation due to the high content of the oily phase, which means that it has a poor stability. In addition, it shows only a poor release of the active ingredient from the preparation. Therefore, it has been urgently required to develop a W/O cream preparation capable of effectively releasing a drug from the viewpoint of pharmacological effects too. Accordingly, it is an object of the present invention to provide a W/O cream preparation which is comfortable in the use, has a high stability and effectively releases the drug.

For instance, when ketotifen having a high chemical activity is added to the conventional cream base, the active ingredient, i.e., ketotifen or its fumarate, reacts with the components of the cream base or impurities contained therein and thus causes a decrease in the content of the active ingredient or a color change with the lapse of time. Furthermore, it is sometimes observed that the cream is degraded into an emulsion or causes liquid separation. In the case of a W/O cream preparation which is inherently inferior to an O/W one in stability, in particular, it is highly difficult to maintain a preparation containing ketotifen or its fumarate in a stable state.

Accordingly, it is another object of the present invention to provide: (1) a stable W/O cream preparation containing ketotifen or its fumarate; and (2) a cream preparation excellent in the percutaneous absorption of ketotifen or its fumarate.

DISCLOSURE OF INVENTION

Under these circumstances, the present inventors have conducted extensive studies and consequently succeeded in achieving the aforesaid objects by providing a W/O cream which contains a much larger amount of moisture than the conventional W/O cream bases. Namely, they have found out that the aforesaid problems can be solved at once by providing a W/O cream preparation consisting of a cream base comprising a diglycerol fatty acid ester and/or a sorbitan fatty acid ester and a polyvalent metal salt of a saturated or unsaturated fatty acid having 10 to 22 carbon atoms, which are used as emulsifiers, an inorganic or organic acid salt, an oily phase component and water together with an active ingredient, thus completing the present invention.

Accordingly, the skin cream preparation for external use of the present invention consists of a cream base comprising from 1 to 10% by weight of a diglycerol fatty acid ester and/or a sorbitan fatty acid ester having an HLB value of from 3 to 7 employed as a surfactant, from 0.01 to 1.0% by weight of a polyvalent metal salt of a saturated or unsaturated fatty acid having 10 to 22 carbon atoms, from 0.1 to 5% by weight of an inorganic or organic acid salt, from 1 to 20% by weight of an oily phase component, and from 70 to 90% by weight of water together with an active ingredient.

Now the present invention will be described in greater detail.

Preferable examples of the active ingredient to be used in the skin cream preparation for external use of the present invention include remedies for skin diseases, such as antiinflammatory agents, antibacterial agents and antiallergic agents. Examples of available antiinflammatory agents include nonsteroidal ones such as ketoprofen, indomethacin, flurbiprofen, felbinac, ibuprofen piconol, benzadac, butyl fulfenamate, bufexamac, piroxicam, loxoprofen, felbinac ethyl, aluminoprofen and oxaprodine and steroidal ones such as clobetasol 17-propionate, dexamethasone 17-valerate, difurazon diacetate, betamethasone 17, 21-dipropionate, diflucortolone 21-valerate, fluocinonide, halcinonide, amcinonide and hydrocortisone 17-butyrate 21-propionate. Examples of the antibacterial agents include tolnaftate, exalamide, tolciclate, siccanin, ciclopirox olamine, clotrimazole, bifonazole, miconazole nitrate, econazole nitrate, omoconazole nitrate, isoconazole nitrate, oxiconazole nitrate, ketoconazole nitrate, itraconazole, fluconazole, butenafine hydrochloride and meticonasole. Examples of the antiallergic agents include ketotifen and its salts, azelastine and its salts, oxatomide, tranilast, sodium chromoglicate, mequitazine, amlexanox, repirinast, oxatomide, ibudilast and glycyrrhetin. Among these compounds, ketotifen and its fumarate are particularly important. These active ingredients may be used in the effective content of each ingredient, namely, from 0.01 to 3% by weight, in the cream preparation. For example, ketotifen or its fumarate may be preferably employed in an amount of from 0.01 to 1% by weight.

In order to produce the W/O cream preparation of the present invention, a diglycerol fatty acid ester and/or a sorbitan fatty acid ester having an HLB (hydrophile/lipophile balance) value of from 3 to 7 are used as a surfactant. Examples of the diglycerol fatty acid ester include diglycerol monooleate, diglycerol monostearate, diglycerol monoisostearate and diglycerol dioleate. Example of the sorbitan fatty acid ester include sorbitan sesquioleate, sorbitan monoisostearate, sorbitan monooleate and sorbitan monostearate. These surfactants may be used in an amount of from 1 to 10% by weight, preferably from 2 to 5% by weight. In addition to these surfactants, other surfactants commonly used for producing a W/O cream may be further used.

Further, a polyvalent metal salt of a saturated or unsaturated fatty acid having 10 to 22 carbon atoms is used in the present invention. Preferable examples of the polyvalent metal salt of a fatty acid include metal salts of fatty acids having 12 to 18 carbon atoms, e.g., aluminum stearate, aluminum palmitate, magnesium stearate, aluminum laurate and aluminum oleate. Among these compounds, aluminum stearate and magnesium stearate are particularly preferable. Although the polyvalent metal salt may be a mono-, di- or tri-metal salt, it is most preferable to select a monometal salt. These polyvalent metal salts of fatty acids may be used in an amount of from 0.01 to 10% by weight, preferably from 0.05 to 0.5% by weight.

Examples of the inorganic or organic acid salt to be used in the present invention include potassium sulfate, magnesium sulfate, sodium sulfate, aluminum sulfate, aluminum nitrate, potassium carbonate, magnesium acetate and potassium acetate. Among these compounds, potassium sulfate and magnesium sulfate are particularly preferable. These inorganic or organic acid salts may be used in an amount of from 0.1 to 5% by weight, preferably from 0.3 to 2% by weight.

Examples of the oily phase component to be used in the present invention include hydrocarbons such as squalane, liquid paraffin and ceresin oil, fatty acid esters such as isopropyl myristate, isopropyl palmitate, diisopropyl sebacate, diethyl sebacate, diisopropyl adipate, glycerol caprate and glycerol caprylate, liquid higher alcohols such as 2-octyldodecanol and 2-hexyldecanol, crotamiton, 1-menthol, mentha oil, benxyl alcohol and silicone oil. These oily phase components may be used in an amount of from 1 to 20% by weight, preferably from 5 to 15% by weight.

The cream preparation of the present invention further contains form 70 to 90% by weight, preferably from 75 to 85% by weight, of water.

In addition to the essential components as cited above, the skin cream preparation for external use of the present invention may further contain appropriate amounts of viscosity modifiers such as carboxyvinyl polymer, hydroxypropylcellulose or polyvinyl alcohol, moistening agents (such as 1,3-butylene glycol, propylene glycol, glycerol or methylbuteanediol, preservatives such as methylparaben, propylparaben or isopropylmethylphenol, or powders such as silicon powder, talc or polystyrene powder (fine pearl), if required.

Now a process for producing the W/O cream preparation of the present invention will be described. The cream preparation of the present invention may be produced in the following manner. First a surfactant, a polyvalent metal salt of a fatty acid, an inorganic or organic acid salt and an oily phase component are melted together by heating to 60° to 80° C. to thereby give an oily phase. Next, water heated to 60° to 80° C. is added to the oily phase and the obtained mixture is emulsified by stirring. Then the mixture is cooled to room temperature under stirring. The active ingredient may be added either to the oily phase or in the emulsification step, followed by stirring.

The production process as mentioned above is merely an example and thus some part thereof may be modified.

BEST MODE FOR CARRYING OUT THE INVENTION

To further illustrate the present invention in greater detail, the following Examples will be given.

EXAMPLE 1

| Component | % by weight |
| --- | --- |
| (1) clotrimazole | 1.0 |
| (2) diglyceryl monooleate | 4.0 |
| (3) aluminum tristearate | 0.08 |
| (4) liquid paraffin | 8.0 |
| (5) isopropyl myristate | 2.0 |
| (6) potassium sulfate | 1.0 |
| (7) methylparaben | 0.2 |
| (8) 1,3-butylene glycol | 2.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antibacterial agent that obtained.

EXAMPLE 2

| Component | % by weight |
| --- | --- |
| (1) clotrimazole | 1.0 |
| (2) diglyceryl monoisostearate | 5.0 |
| (3) aluminum tristearate | 0.08 |
| (4) liquid paraffin | 6.0 |
| (5) isopropyl myristate | 2.0 |
| (6) magnesium sulfate | 1.0 |
| (7) methylparaben | 0.2 |
| (8) propylene glycol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antibacterial agent was obtained.

EXAMPLE 3

| Component | % by weight |
| --- | --- |
| (1) bifonazole | 1.0 |
| (2) diglyceryl monooleate | 5.0 |

-continued

| Component | % by weight |
|---|---|
| (3) aluminum tristearate | 0.08 |
| (4) squalane | 8.0 |
| (5) diisopropyl sebacate | 2.0 |
| (6) magnesium sulfate | 1.0 |
| (7) methylpolysiloxane | 0.2 |
| (8) propylene glycol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antibacterial agent was obtained.

EXAMPLE 4

| Component | % by weight |
|---|---|
| (1) clobetasol 17-propionate | 0.05 |
| (2) diglyceryl monooleate | 5.0 |
| (3) aluminum monostearate | 0.08 |
| (4) squalane | 8.0 |
| (5) isopropyl myristate | 2.0 |
| (6) magnesium sulfate | 1.0 |
| (7) methylparaben | 0.2 |
| (8) propylene glycol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing a steroidal antiinflammatory agent was obtained.

Example 5

| Component | % by weight |
|---|---|
| (1) fuluocinonide | 0.05 |
| (2) diglyceryl monooleate | 5.0 |
| (3) aluminum monostearate | 0.08 |
| (4) squalane | 8.0 |
| (5) talc | 2.0 |
| (6) mangesium sulfate | 1.0 |
| (7) methylparaben | 0.2 |
| (8) propylene glycol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby given an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing a steroidal antiinflammatory agent was obtained.

EXAMPLE 6

| Component | % by weight |
|---|---|
| (1) fluocinonide | 0.05 |
| (2) diglyceryl monooleate | 5.0 |
| (3) aluminum tristearate | 0.08 |
| (4) liquid parafin | 8.0 |
| (5) fine pearl | 2.0 |
| (6) potassium sulfate | 1.0 |
| (7) methylparaben | 0.3 |
| (8) glycerol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing a steroidal antiinflammatory agent was obtained.

EXAMPLE 7

| Component | % by weight |
|---|---|
| (1) clobetasol 17-propionate | 0.05 |
| (2) sorbitan monoisostearate | 5.0 |
| (3) aluminum tristearate | 0.08 |
| (4) squalane | 8.0 |
| (5) diethyl cebacate | 2.0 |
| (6) potassium sulfate | 1.0 |
| (7) methylparaben | 0.2 |
| (8) propylene glycol | 3.0 |
| (9) purified water | the balance |
| in total | 100.00 |

The components (2) and (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing a steroidal antiinflammatory agent was obtained.

EXAMPLE 8

| Component | % by weight |
|---|---|
| (1) ketoprofen | 0.5 |
| (2) diglyceryl monooleate | 5.0 |
| (3) aluminum tristearate | 0.08 |
| (4) liquid paraffine | 8.0 |
| (5) fine pearl | 2.0 |
| (6) potassium sulfate | 1.0 |
| (7) methylparaben | 0.3 |
| (8) glycerol | 3.0 |
| (9) purified water | the balance |
| in total | 100.00 |

The components (2) to (5) were melted by heating to 70° C. to thereby give an oily phase. Separately, the components (6) to (9) were dissolved by heating to 70°

C. to thereby given an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing a nonsteroidal antiinflammatory agent was obtained.

EXAMPLE 9

| Component | % by weight |
|---|---|
| (1) indomethacin | 0.5 |
| (2) diglyceryl monooleate | 5.0 |
| (3) magnecium monostearate | 0.1 |
| (4) squalane | 8.0 |
| (5) methylpolysiloxane | 0.2 |
| (6) octyldodecyl myristate | 2.0 |
| (7) potassium sulfate | 1.0 |
| (8) methylparabene | 0.2 |
| (9) glycerol | 3.0 |
| (10) purified water | the balance |
| in total | 100.00 |

The components (2) to (6) were melted by heating to 70° C. to thereby give an oily phase. Separately, the components (6) to (10) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing a nonsteroidal antiinflammatory agent was obtained.

EXAMPLES 10

| Component | % by weight |
|---|---|
| (1) loxoprofen | 1.0 |
| (2) diglyceryl monoisostearate | 5.0 |
| (3) magnesium monostearate | 0.1 |
| (4) liquid paraffine | 8.0 |
| (5) isopropyl myristate | 0.2 |
| (6) magnesium sulfate | 1.0 |
| (7) methylparaben | 0.2 |
| (8) glycerol | 4.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring, Next, the component (1) was added thereto and dispersed therein by stirring. The mixture was cooled to room temperature under further stirring. Thus a cream preparation containing a nonsteroidal antiinflammatory agent was obtained.

EXAMPLE 11

| Component | % by weight |
|---|---|
| (1) ketofifen fumarate | 0.5 |
| (2) diglyceryl monooleate | 5.0 |
| (3) aluminium tristearate | 0.08 |
| (4) liquid paraffine | 8.0 |
| (5) fine pearl | 2.0 |
| (6) potassium sulfate | 1.0 |
| (7) methylparaben | 0.3 |
| (8) glycerol | 3.0 |
| (9) purified water | the balance |
| in total | 100.00 |

The components (2) to (4) were melted by heating to 70° C. to thereby give an oily phase. Separately, the component (1) and components (5) to (9) were dissolved by heating to 70° C. to thereby give an aqueous phase. Then the aqueous phase was added to the oily phase and the obtained mixture was emulsified by stirring. Next, the mixture was cooled to room temperature under further stirring. Thus a cream preparation containing an antiallergic agent was obtained.

EXAMPLE 12

| Component | % by weight |
|---|---|
| (1) ketotifen | 0.1 |
| (2) diglyseryl monoisostearate | 4.0 |
| (3) aluminium monostearate | 0.08 |
| (4) liquid paraffine | 8.0 |
| (5) isopropyl myristate | 2.0 |
| (6) potassium sulfate | 1.0 |
| (7) methylparaben | 0.2 |
| (8) propylene glycol | 2.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antiallergic agent was obtained.

EXAMPLE 13

| Component | % by weight |
|---|---|
| (1) ketotiphen | 0.1 |
| (2) sorbitan monoisostearate | 5.0 |
| (3) aluminium monostearate | 0.08 |
| (4) liquid paraffine | 6.0 |
| (5) isopropyl myristate | 2.0 |
| (6) magnesium sulfate | 1.0 |
| (7) methylparaben | 0.2 |
| (8) 1,3-butylene glycol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antiallergic agent was obtained.

EXAMPLE 14

| Component | % by weight |
|---|---|
| (1) ketotifen | 0.3 |
| (2) diglyceryl monooleate | 5.0 |
| (3) aluminium monostearate | 0.12 |
| (4) squalane | 8.0 |
| (5) isopropyl sebacate | 2.0 |
| (6) magnesium sulfate | 1.0 |
| (7) methylpolysiloxane | 0.2 |
| (8) propylene glycol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antiallergic agent was obtained.

EXAMPLE 15

| Component | % by weight |
|---|---|
| (1) ketotifen | 0.05 |
| (2) diglyceryl monoisostearate | 5.0 |
| (3) aluminium tristearate | 0.08 |
| (4) squalane | 8.0 |
| (5) isopropyl myristate | 2.0 |
| (6) magnesium sulfate | 1.0 |
| (7) methylparaben | 0.2 |
| (8) propylene glycol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antiallergic agent was obtained.

EXAMPLE 16

| Component | % by weight |
|---|---|
| (1) ketotifen fumarate | 0.1 |
| (2) diglyceryl monooleate | 5.0 |
| (3) aluminium tristearate | 0.08 |
| (4) squalane | 8.0 |
| (5) talc | 2.0 |
| (6) magnesium sulfate | 1.0 |
| (7) methylparaben | 0.2 |
| (8) glycerol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antiallergic agent was obtained.

EXAMPLE 17

| Component | % by weight |
|---|---|
| (1) ketotifen | 0.2 |
| (2) diglyceryl monooleate | 5.0 |
| (3) aluminium monostearate | 0.08 |
| (4) liquid paraffin | 8.0 |
| (5) fine pearl | 2.0 |
| (6) potassium sulfate | 1.0 |
| (7) methylparaben | 0.3 |
| (8) glyceryl | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antiallergic agent was obtained.

EXAMPLE 18

| Component | % by weight |
|---|---|
| (1) ketotifen | 0.1 |
| (2) diglyceryl monoisostearate | 5.0 |
| (3) aluminium monostearate | 0.08 |
| (4) squalane | 8.0 |
| (5) isopropyl myristate | 2.0 |
| (6) potassium sulfate | 1.0 |
| (7) methylparaben | 0.2 |
| (8) propylene glycol | 3.0 |
| (9) carboxyvinylpolymer | 0.05 |
| (10) purified water | the balance |
| in total | 100.00 |

The components (2) to (5) were melted by heating to 70° C. to thereby give an oily phase. Separately, the components (6) to (8) and a part of the components (10) were dissolved by heating to 70° C. to thereby give an aqueous phase. Then the aqueous phase was added to the oily phase and the obtained mixture was emulsified by stirring. Next, the component (9), which was swelled by the residue of the components (10), was added to the thus obtained emulsion and further the component (1) was added thereto and dispersed therein by stirring. The mixture was cooled to room temperature under further stirring. Thus a cream preparation containing an antiallergic agent was obtained.

EXAMPLE 19

| Component | % by weight |
|---|---|
| (1) ketotifen fumarate | 0.188 |
| (2) diglyceryl monoisostearate | 4.0 |
| (3) magnesium monostearate | 0.1 |
| (4) squalane | 8.0 |
| (5) isopropyl myristate | 1.5 |
| (6) potassium sulfate | 1.0 |
| (7) methylparaben | 0.15 |
| (8) fine pearl | 1.0 |

-continued

| Component | % by weight |
|---|---|
| (9) propylene glycol | 3.0 |
| (10) purified water | the balance |
| in total | 100.00 |

The components (2) to (5) were melted by heating to 70° C. to thereby give an oily phase. Separately, the components (6) to (10) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antiallergic agent was obtained.

REFERENCE EXAMPLE 1

| Component | % by weight |
|---|---|
| (1) clotrimazole | 1.0 |
| (2) hexaglyceryl polyricinolate | 5.0 |
| (3) aluminium tristearate | 0.08 |
| (4) liquid paraffin | 8.0 |
| (5) fine pearl | 2.0 |
| (6) potassium sulfate | 1.0 |
| (7) methylparaben | 0.3 |
| (8) glycerol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antibacterial agent was obtained.

REFERENCE EXAMPLE 2

| Component | % by weight |
|---|---|
| (1) clotrimazole | 1.0 |
| (2) decaglyceryl pentaoleate | 5.0 |
| (3) aluminium tristearate | 0.08 |
| (4) liquid paraffin | 8.0 |
| (5) octyldodecyl myristate | 2.0 |
| (6) potassium sulfate | 1.0 |
| (7) methylparaben | 0.3 |
| (8) glycerol | 3.0 |
| (9) purified water | the balance |
| in total | 100.00 |

The components (2) to (5) were melted by heating to 70° C. to thereby give an oily phase. Separately, the components (6) to (9) were dissolved by heating to 70° C. to thereby give an aqueous phase. Then the aqueous phase was added to the oily phase and the obtained mixture was emulsified by stirring. Next, the component (1) was added thereto and dispersed therein by stirring. The mixture was cooled to room temperature under further stirring. Thus a cream preparation containing an antibacterial agent was obtained.

REFERENCE EXAMPLE 3

| Component | % by weight |
|---|---|
| (1) ketotifen | 0.1 |
| (2) white petrolatum | 40.0 |
| (3) cetanol | 10.0 |
| (4) white beeswax | 5.0 |
| (5) sorbitan sesquioleate | 5.0 |
| (6) lauromacrogol | 0.5 |
| (7) methylparaben | 0.1 |
| (8) propyl parabene | 0.1 |
| (9) purified water | the balance |
| in total | 100.00 |

The components (2) to (6) were melted by heating to 70° C. to thereby give an oily phase. Separately, the components (7) to (9) were dissolved by heating by 70° C. to thereby give an aqueous phase. Then the aqueous phase was added to the oily phase and the obtained mixture was emulsified by stirring. Next, after cooling the thus obtained emulsion to 40° C., the component (1) was added thereto and dispersed therein by stirring. The mixture was cooled to room temperature under further stirring. Thus a cream preparation containing an antiallergic agent was obtained.

TEST EXAMPLE 1

Heat stability test A

The cream preparation of the Example 1 and the one of the Reference Example 1 were each packed in a tube and stored at 40° C. and 50° C. Thus the heat stability of each product was evaluated. Table 1 shows the results.

TABLE 1

| | Heat stability test for cream preparation | | | | |
|---|---|---|---|---|---|
| | 40° C. | | | 50° C. | |
| | 1 month | 2 months | 3 months | 1 month | 2 months |
| Cream of Ex. 1 | no change | no change | no change | no change | no change |
| Cream of Ref. Ex. 1 | liquid separation | — | — | liquid separation | — |
| Cream of Ref. Ex. 2 | no change | no change | no change | no change | liquid separation |

As is apparent from Table 1, the cream preparation of the Example 1 remained highly stable after being stored at 40° C. and 50° C., compared with those of the Reference Examples 1 and 2 containing different surfactants.

Heat stability test B

The cream preparation of the Examples 12 and 13 and the one of the Reference Example 3 were each packed in a tube and stored at 50° C. Thus the heat stability of each product was evaluated. Table 2 shows the results.

TABLE 2

| | Heat stability test for cream preparation | | | | |
|---|---|---|---|---|---|
| | 50° C. (change in appearance) | | | 50° C. (residue %) | |
| | 1 week | 2 weeks | 1 month | 15 days | 30 days |
| Cream of Ex. 12 | no change | no change | no change | 98.8 | 96.7 |
| Cream of Ex. 13 | no change | no change | no change | 97.7 | 95.9 |
| Cream of | liquid | — | — | — | — |

TABLE 2-continued

| Heat stability test for cream preparation | | | | |
|---|---|---|---|---|
| | 50° C. (change in appearance) | | 50° C. (residue %) | |
| | 1 week | 2 weeks | 1 month | 15 days | 30 days |
| Ref. Ex. 3 | separation | | | | |

As is apparent from Table 2, the properties of the active ingredients and the cream preparations of the Examples 12 and 13 remained highly stable after being stored at 50° C., compared with that of the Reference Example 3 produced by using the conventional W/O type cream base.

TEST EXAMPLE 2 RELEASE TEST

The cream preparation of the Example 1 and a commercially available cream preparation containing clotrimazole were subjected to a release test by the following test method. Table 3 (polycarbonate film) and Table 4 (silicone film) show the results.

Test method

A sample was introduced into a glass disk (diameter: 20 mm, thickness: 2 mm) and the surface was covered with a film, followed by fixing with an O ring. This disk was introduced into a mesh bag and immersed in a releasing solution. Then the amount of clotrimazole liberated from the sample, under stirring, was determined by liquid chromatography.

TABLE 3

| Release test (polycarbonate film): expressed in release ratio | | | | | |
|---|---|---|---|---|---|
| | Time (hr) | | | | |
| Preparation | 0 | 2 | 4 | 6 | 8 |
| *A | 0 | 4.63 | 8.11 | 11.3 | 14.63 |
| **B | 0 | 1.25 | 1.81 | 2.05 | 2.37 |

*A: the cream preparation of the Example 1.
**B: the marketed cream preparation.

Elution conditions

Film: polycarbonate (pore size = 10 μm).
Temperature: 37° C.
Solvent: 30% methanol, 200 ml.
Amount of sample: 1 ml.

TABLE 4

| Release test (silicone film): expressed in release ratio | | | |
|---|---|---|---|
| | Time (hr) | | |
| Preparation | 0 | 2 | 4 | 8 |
| *A | 0 | 5.63 | 10.15 | 14.05 |
| **B | 0 | 0.87 | 1.03 | 1.63 |

*A: the cream preparation of the Example 1.
**B: the marketed cream preparation.

Elution conditions

Film: silicone (polydimethylsiloxane, a product of Dow Corning Co.)
Temperature: 37° C.
Solvent: 30% methanol, 200 ml.
Amount of sample: 1 ml.

As the above Tables 3 and 4 clearly show, the cream preparation (A) of the present invention of the Example 1 was superior in the drug-releasing properties to the commercially available O/W cream preparation (B).

TEST EXAMPLE 3

Skin permeation test on hairless mouse

Test method

The skin of a hairless mouse was peeled off and introduced into a Franz-type diffusion cell (application area: 0.785 cm$^2$, capacity of receptor phase: 5 ml) in such a manner that the corneal layer side served as the donor phase. 5 ml of a 50 mM phosphate buffer solution (pH: 7.4)/physiological saline (PBS) containing 10% of ethanol was fed into the receptor phase as a receptor solution. Next, the receptor solution was sampled in 0.5-ml portions at given time intervals and the same amount of the receptor solution was supplied after each sampling procedure. To the receptor solution, 0.025% of sodium azide was added as a preservative.

The dose of a sample was determined in the following manner. Namely, the cell containing the hairless mouse skin was first weighed. After administering the sample to the donor phase, the cell was weighed again. Thus the difference was defined as the dose of the sample. The dose of the sample was 30 mg±5%. Then the ketotifen contained in the receptor solution was determined by HPLC after 4 hours and 8 hours.

The ketotifen pooled in the skin was determined by the following method. After the completion of the sampling in the aforesaid skin permeation test, the skin was taken out of the cell and the sample on the surface thereof was wiped away with methanol. Then the skin was put into a centrifugal tube containing methanol and cut into small pieces with scissors. Then it was homogenized in a homogenizer and shaken in a shaker for 30 minutes to thereby extract the ketotifen from the skin into the methanol. After filtering and filling up to 50 ml, a sample for determining the ketotifen pooled in the skin was obtained. Then the ketotifen pooled in the skin was determined by HPLC at the UV wavelength of 297 nm.

Table 5 and 6 show the results.

HPLC conditions

Wavelength: 297 nm (UV).
Device: LC-6A (Shimadzu Seisakusho).
Mobile phase: MeOH/(0.05M) borax (0.1M) KH$_2$PO$_4$ buffer solution (pH: 9.0) = 6.5/3.5.
Column temperature: 40° C.
Column: Capsule Pack C-18 SG-120 (Shiseido).

The skin permeation ratio was calculated in accordance with the following equation:

$$\text{skin permeation ratio (\%)} = \frac{\text{drug permeation into receptor}}{\text{drug dose}} \times 100$$

Test result

1. Skin permeation ratio (%)

TABLE 5

| Permeation ratio of ketotifen into hairless mouse skin | | |
|---|---|---|
| | 4 hours | 8 hours |
| Cream preparation of Ex. 12 | 6.48** | 28.52** |
| Cream preparation of Ex. 13 | 3.81* | 18.16* |
| Cream preparation of Ref. Ex. 3 | 1.92 | 7.08 |

*: P < 0.05.
**: P < 0.01.

Thus it was found out that the cream preparations of the Examples 12 and 13 showed significant differences respectively at significant levels (P) of less than 1% and less than 5%, from the cream preparation of the Reference Example 3 (according to the t-test).

2. Pool ratio in skin

TABLE 6

| Pool ratio of ketotifen in hairless mouse skin | |
|---|---|
| | Pool ratio in skin (%) |
| Cream preparation of Ex. 12 | 24.83** |
| Cream preparation of Ex. 13 | 16.80** |
| Cream preparation of Ref. Ex. 3 | 2.63 |

**: $P < 0.01$

Thus it was found out that the cream preparations of the Examples 12 and 13 showed each a significant difference at a significant level (P) of less than 1%, from the cream preparation of the Reference Example 3 (according to the t-test).

As is apparent from Tables 5 and 6, the cream preparations of the present invention obtained in the Examples 12 and 13 were significantly superior in the permeability into the hairless mouse skin and the pool properties of ketotifen in the skin to the cream preparation of the Reference Example 1 produced by using the conventional cream base.

Industrial Applicability

The W/O cream preparation of the present invention has a high heat stability and suffers from neither liquid separation nor any change in appearance even when stored for a long time. Further, it contains less oily phase components and a larger amount of water and thus is less sticky and nongreasy, so that it is excellent in the comfortableness in the use. Furthermore, this cream preparation has a good adhesiveness to the skin and efficiently releases the active ingredient, which makes it preferable from the pharmacological viewpoint too.

For example, a cream preparation of the present invention particularly containing ketotifen has a high heat stability and suffers from neither liquid separation nor any change in the appearance or the active ingredient even after prolonged storage. Further, it contains less oily phase components and a larger amount of water and thus is less sticky and nongreasy, so that it is excellent in the comfortableness in the use. Furthermore, this cream preparation is excellent in the adhesiveness to the skin and the percutaneous absorption of the active ingredient, which makes it preferable from the pharmacological viewpoint too.

Accordingly, the cream preparation of the present invention containing, for example, an antiinflammatory agent, an antiallergic agent or an antibacterial agent is highly useful as a remedy for skin diseases such as dermatitis, eczema, trichophytia, candidiasis, chromophytosis and atopic eczema.

We claim:

1. A W/O skin cream preparation for external use consisting of (A) a cream consisting of a) from 1 to 10% by weight of at least one member selected from the group of diglycerol monoisostearate and diglycerol monooleate having an HLB value of from 3 to 7, b) from 0.01 to 1.0% by weight of a polyvalent metal salt of a saturated or unsaturated fatty acid having 10 to 22 carbon atoms, c) from 0.1 to 5% by weight of an inorganic or organic acid salt, d) from 1 to 20% by weight of an oily phase component, e) from 2 to 3% by weight of a moistening agent which is a member selected from the group of glycerol, propylene glycol and 1,3-butylene glycol, f) from 0.15 to 0.3% by weight of methyl paraben as a preservative, g) from 70 to 90% by weight of water, and (B) as the pharmaceutically active either omoconazole nitrate or ketotifen or ketotifen fumarate.

2. A W/O skin cream preparation for external use consisting of (A) a cream consisting of a) from 1 to 10% by weight of at least one member selected from the group of diglycerol monoisostearate and diglycerol monooleate having an HLB value of from 3 to 7, b) from 0.01 to 1.0% by weight of a polyvalent metal salt of a saturated or unsaturated fatty acid having 10 to 22 carbon atoms, c) from 0.1 to 5% by weight of an inorganic or organic acid salt, d) from 1 to 20% by weight of an oily phase component, e) from 2 to 3% by weight of a moistening agent which is a member selected from the group of glycerol, propylene glycol and 1,3-butylene glycol, f) from 0.15 to 0.3% by weight of methyl paraben as a preservative, g) from 70 to 90% by weight of water (h) 0.05% by weight of a viscosity modifier which is a member selected from the group of a carboxyvinyl polymer, hydroxypropyl cellulose and polyvinyl alcohol and B) as the pharmaceutically active agent either omoconazole nitrate or ketotifen or ketotifen fumarate.

3. A W/O skin cream preparation for external use consisting of (A) a cream consisting of a) from 1 to 10% by weight of at least one member selected from the group of diglycerol monoisostearate and diglycerol monooleate having an HLB value of from 3 to 7, b) from 0.01 to 1.0% by weight of a polyvalent metal salt of a saturated or unsaturated fatty acid having 10 to 22 carbon atoms, c) from 0.1 to 5% by weight of an inorganic or organic acid salt, d) from 1 to 20% by weight of an oily phase component, e) from 2 to 3% by weight of a moistening agent which is a member selected from the group of glycerol, propylene glycol and 1,3-butylene glycol, f) from 0.15 to 0.3% by weight of methyl paraben as a preservative, g) from 70 to 90% by weight of water, h) 1% by weight of a powder which is a member selected from the group consisting of silicon powder, talc and polystyrene powder, and B) as the pharmaceutically active agent either omoconazole nitrate or ketotifen or ketotifen fumarate.

4. The composition according to claim 1 wherein said diglycerol monoisostearate and said diglycerol monooleate exhibit HLB value of 5.5.

5. A W/O skin cream preparation according to claim 1, wherein the content of said pharmaceutically active agent ranges from 0.01 to 3% by weight.

6. The W/O skin cream preparation according to claim 1, wherein said polyvalent metal salt of said saturated or unsaturated fatty acid is at least one member selected from the group consisting of aluminum mono-, di- or tri-stearate and magnesium mono-, di- or tri-stearate.

7. The W/O skin cream preparation according to claim 1, wherein said inorganic or organic acid salt is at least one member selected from the group consisting of potassium sulfate, magnesium sulfate, sodium sulfate, aluminum sulfate, aluminum nitrate, potassium carbonate, magnesium acetate and potassium acetate.

8. The W/O skin cream preparation according to claim 1, wherein said oily phase component is at least one member selected from the group consisting of squalane, liquid paraffin, ceresin oil, isopropyl myristate, isopropyl palmitate, diisopropyl sebacate, diethyl sebacate, diisopropyl adipate, glycerol caprate, glycerol caprylate, 2-octyldodecanol, 2-hexyldecanol, crotamiton, 1-menthol, mentha oil, benzyl alcohol and silicone oil.

* * * * *